(12) United States Patent
Thompson et al.

(10) Patent No.: US 7,875,608 B2
(45) Date of Patent: Jan. 25, 2011

(54) SUBSTITUTED 8-[6-AMINO-3PYRIDYL]XANTHINES

(76) Inventors: Robert D. Thompson, P.O. Box 4632, Charlottesville, VA (US) 22905; Guoquan Wang, P.O. Box 4632, Charlottesville, VA (US) 22905; Anthony Beauglehole, P.O. Box 4632, Charlottesville, VA (US) 22905; Frank Schmidtmann, P.O. Box 4632, Charlottesville, VA (US) 22905

( * ) Notice: Subject to any disclaimer, the term of this patent is extended or adjusted under 35 U.S.C. 154(b) by 7 days.

(21) Appl. No.: 12/337,010

(22) Filed: Dec. 17, 2008

(65) Prior Publication Data

US 2009/0163491 A1  Jun. 25, 2009

Related U.S. Application Data

(60) Provisional application No. 61/014,134, filed on Dec. 17, 2007.

(51) Int. Cl.
C07D 473/06 (2006.01)
A61K 31/522 (2006.01)
A61P 11/06 (2006.01)
A61P 27/02 (2006.01)
C07D 401/12 (2006.01)

(52) U.S. Cl. ............... 514/234.2; 514/263.22; 544/118; 544/269; 544/310

(58) Field of Classification Search ............. 514/234.2, 514/263.22; 544/118, 269
See application file for complete search history.

(56) References Cited

U.S. PATENT DOCUMENTS

| | | | | |
|---|---|---|---|---|
| 6,117,878 A | * | 9/2000 | Linden | 514/263.34 |
| 6,894,021 B2 | * | 5/2005 | Belardinelli et al. | 514/1 |
| 7,317,017 B2 | * | 1/2008 | Kalla et al. | 514/263.2 |
| 7,342,006 B2 | * | 3/2008 | Wang et al. | 514/211.08 |
| 7,579,348 B2 | * | 8/2009 | Wang et al. | 514/234.2 |
| 7,598,379 B2 | * | 10/2009 | Wang et al. | 544/269 |
| 7,601,723 B2 | * | 10/2009 | Wang et al. | 514/255.05 |
| 2007/0219221 A1 | * | 9/2007 | Zeng et al. | 514/263.2 |
| 2008/0004292 A1 | * | 1/2008 | Wang et al. | 514/263.22 |

* cited by examiner

*Primary Examiner*—Mark L Berch
(74) *Attorney, Agent, or Firm*—McCarter & English, LLP

(57) ABSTRACT

The present invention provides substituted 8-[6-amino-3-pyridyl]xanthines like the compound shown in the following formula:

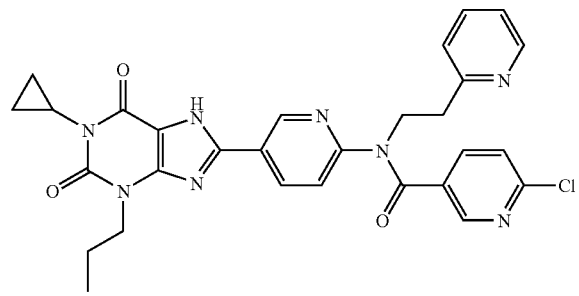

and pharmaceutical compositions that are selective antagonists of $A_{2B}$ adenosine receptors (ARs). These compounds and compositions are useful as pharmaceutical agents.

24 Claims, No Drawings

SUBSTITUTED 8-[6-AMINO-3PYRIDYL]XANTHINES

CROSS-REFERENCE TO RELATED APPLICATIONS

This present application claims the priority benefits of U.S. Provisional Application No. 61/014,134, filed Dec. 17, 2007, which is expressly incorporated fully herein by reference.

STATEMENT OF GOVERNMENT RIGHTS

This invention was made with the assistance of government support under United States Grant No. 5 R44 AI048979-03 from the National Institutes of Health. The government may have certain rights to the invention.

FIELD OF THE INVENTION

The present invention relates to substituted 8-[6-amino-3-pyridyl]xanthines and pharmaceutical compositions that are selective antagonists of $A_{2B}$ adenosine receptors (ARs). These compounds and compositions are useful as pharmaceutical agents.

BACKGROUND OF THE INVENTION

The alkylxanthine theophylline (below), a weak non-selective adenosine

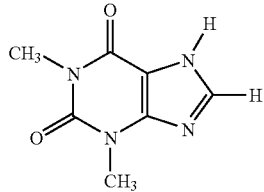

antagonist (See Linden, J., et al., *Cardiovascular Biology of Purines*, eds. G. Burnstock, et al., 1998, pp 1-20), is useful therapeutically for the treatment of asthma. However, its use is associated with unpleasant side effects, such as insomnia and diuresis. In recent years, the use of theophylline as a bronchodilator, for relief of asthma, has been supplanted by drugs of other classes, e.g, selective $\beta_2$-adrenergic agonists, corticosteroids, and recently leukotriene antagonists. These compounds also have limitations. Thus, the development of a theophylline-like drug with reduced side effects is still desirable.

It has been recognized that theophylline and its closely related analogue caffeine block endogenous adenosine acting as a local modulator of adenosine receptors in the brain and other organs at therapeutically useful doses. Adenosine activates four subtypes of G protein-coupled adenosine receptors (ARs), $A_1/A_{2A}/A_{2B}/A_3$. Enprofylline (below) is another example of a xanthine that has been reported to block $A_{2B}$ adenosine receptors and is used

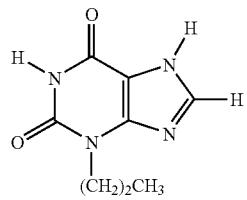

to treat asthma. It has also been shown by LaNoue et al (U.S. Pat. No. 6,060,481) that selective adenosine $A_{2B}$ antagonists are useful for improving insulin sensitivity in a patient.

It has been reported that therapeutic concentrations of theophylline or enprofylline block human $A_{2B}$ receptors, and it has been proposed that antagonists selective for this subtype may have potential use as antiasthmatic agents. (See Feoktistov, I., et al., *Pharmacol. Rev.* 1997, 49, 381-402; and Robeva, A. S., et al., *Drug Dev. Res.* 1996, 39, 243-252). Enprofylline has a reported $K_i$ value of 7 µM and is somewhat selective in binding to human $A_{2B}$ ARs. (See Robeva, A. S., et al., *Drug Dev. Res.* 1996, 39, 243-252 and Linden, J., et al., *Mol. Pharmacol.* 1999, 56, 705-713). $A_{2B}$ ARs are expressed in some mast cells, such as the BR line of canine mastocytoma cells, which appear to be responsible for triggering acute $Ca^{2+}$ mobilization and degranulation. (See Auchampach, J. A., et al., *Mol. Pharmacol*, 1997, 52, 846-860 and Forsyth, P., et al., *Inflamm. Res.* 1999, 48, 301-307). $A_{2B}$ ARs also trigger $Ca^{2+}$ mobilization, and participate in a delayed IL8 release from human HMC-1 mast cells. Other functions associated with the $A_{2B}$ AR are the control of cell growth and gene expression, (See Neary, J., et al., *Trends Neurosci.* 1996, 19, 13-18) endothelial-dependent vasodilation (See Martin, P. L., et al., *J. Pharmacol. Exp. Ther.* 1993, 265, 248-253), and fluid secretion from intestinal epithelia. (See Strohmeier, G. R., et al., *J. Biol. Chem.* 1995, 270, 2387-2394). Adenosine acting through $A_{2B}$ ARs has also been reported to stimulate chloride permeability in cells expressing the cystic fibrosis transport regulator. (See Clancy, J. P., et al., *Am. J. Physiol.* 1999, 276, C361-C369.)

Recently Linden et al (U.S. Pat. No. 6,545,002) have described a new group of compounds and pharmaceutical compositions that are selective antagonists of $A_{2B}$ adenosine receptors (ARs).

Although adenosine receptor subtype-selective probes are available for the $A_1$, $A_{2A}$, and $A_3$ ARs, only few selective antagonists are known for the $A_{2B}$ receptor. Therefore, a continuing need exists for compounds that are selective $A_{2B}$ receptor antagonists.

SUMMARY OF THE INVENTION

The present invention provides substituted 8-[6-amino-3-pyridyl]xanthines or stereoisomers or pharmaceutically acceptable salts that act as antagonists of $A_{2B}$ adenosine receptors.

The invention also provides pharmaceutical compositions comprising a compound of the present invention or stereoisomer or a pharmaceutically acceptable salt thereof in combination with a pharmaceutically acceptable excipient.

Additionally, the invention provides a therapeutic method for treating a pathological condition or symptom in a mammal, such as a human, wherein the activity, e.g., over-activity, of adenosine $A_{2B}$ receptors is implicated in one or more symptoms of the pathology and antagonism (i.e., blocking) is desired to ameliorate such symptoms. Thus, the present invention provides a method of treating a disease comprising administering a therapeutically effective amount of at least one compound of the present invention or a stereoisomer or pharmaceutically acceptable salt thereof, wherein the disease is selected from asthma, allergies, allergic diseases (e.g., allergic rhinitis and sinusitis), autoimmune diseases (e.g., lupus), diarrheal diseases, insulin resistance, diabetes (e.g., Type I and Type II), prevention of mast cell degranulation associated with ischemia/reperfusion injuries, heart attack, inhibition of angiogenesis in neoplastic tissues, and inhibition of angiogenesis in diabetic retinopathy or hyperbaric oxygen-induced retinopathy.

The invention provides a novel compound of the present invention for use in medical therapy.

The invention also provides the use of a novel compound of the present invention for the manufacture of a medicament for the treatment of a pathological condition or symptom in a mammal, which is associated with deleterious $A_{2B}$ receptor activation or activity.

The invention also includes a method comprising contacting a compound of the present invention, optionally having a radioactive isotope (radionuclide), such as, for example, tritium, radioactive iodine (e.g., $^{125}I$ for binding assays or $^{123}I$ for Spectral Imaging) and the like, with target $A_{2B}$ adenosine receptor sites comprising said receptors, in vivo or in vitro, so as to bind to said receptors. Cell membranes comprising bound $A_{2B}$ a adenosine receptor sites can be used to measure the selectivity of test compounds for adenosine receptor subtypes or can be used as a tool to identify potential therapeutic agents for the treatment of diseases or conditions associated with $A_{2B}$-receptor mediation, by contacting said agents with said radioligands and receptors, and measuring the extent of displacement of the radioligand and/or binding of the agent.

DETAILED DESCRIPTION OF THE INVENTION

Applicants have discovered that the substituted 8-[6-amino-3-pyridyl]xanthines shown below can be useful for the treatment diseases or conditions associated with deleterious $A_{2B}$ receptor activation or activity.

In an aspect of the invention, there is provided a compound selected from:

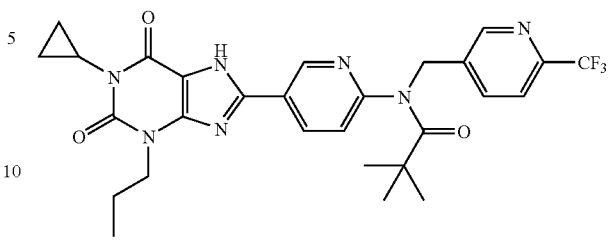

1

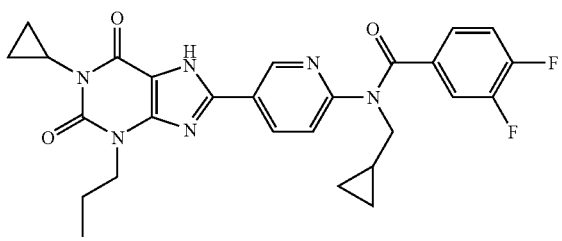

2

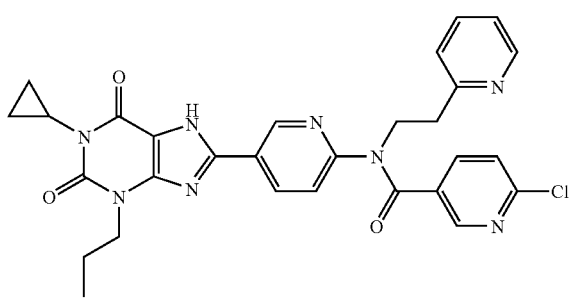

3

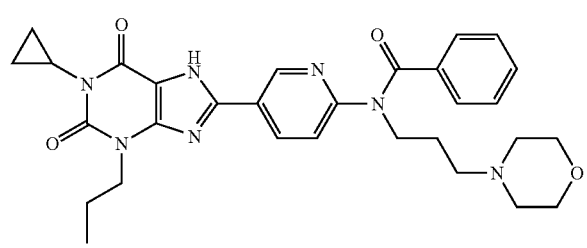

4

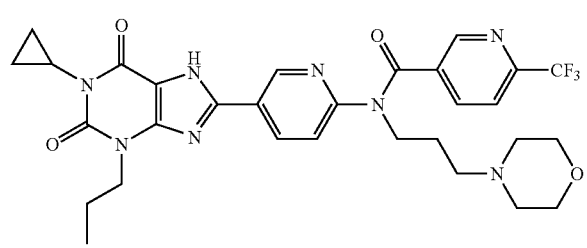

5

6 or a stereoisomer or pharmaceutically acceptable salt thereof.

In another aspect of the invention, there is provided a pharmaceutical composition comprising: (a) a therapeutically effective amount of a compound described above; and (b) a pharmaceutically acceptable excipient.

In another aspect of the invention, there is provided a therapeutic method for preventing or treating a pathological condition or symptom in a mammal, wherein the activity of adenosine $A_{2B}$ receptors is implicated and antagonism of its action is desired comprising administering to the mammal a therapeutically effective amount of a compound of the present invention.

In another aspect of the invention, there is provided a method of treating a disease comprising administering a therapeutically effective amount of at least one compound of the present invention or a stereoisomer or pharmaceutically acceptable salt thereof, wherein the disease is selected from asthma, allergies, allergic diseases (e.g., allergic rhinitis and sinusitis), autoimmune diseases (e.g., lupus), diarrheal diseases, insulin resistance, diabetes, prevention of mast cell degranulation associated with ischemia/reperfusion injuries, heart attack, inhibition of angiogenesis in neoplastic tissues, and inhibition of angiogenesis in diabetic retinopathy or hyperbaric oxygen-induced retinopathy.

In another aspect of the invention, there is provided the compound of the present invention for use in medical therapy.

In another aspect, there is provided a use of a compound of the invention, for the manufacture of a medicament useful for the treatment of a disease in a mammal.

It is understood that any aspect or feature of the present invention whether characterized as preferred or not characterized as preferred may be combined with any other aspect or feature of the invention, whether such other feature is characterized as preferred or not characterized as preferred.

As is recognized by one of ordinary skill in the art, the imidazole ring of the compounds of the present invention may exist in tautomeric forms or as tautomers, and thus are also included within the scope of the invention. The tautomeric isomers are represented as the structures (Ia) and (Ib):

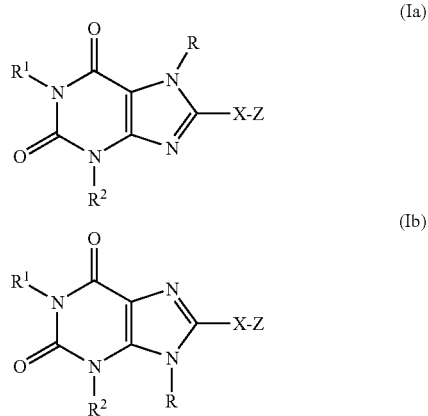

wherein R, $R^1$, $R^2$, X, and Z are as defined herein.

By naming or referring to one compound, for example, it is understood for the purposes of the present application that its corresponding tautomer is also intended.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

It will be appreciated by those skilled in the art that compounds of the invention having a chiral center may exist in and be isolated in optically active, and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein; it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine therapeutic activity using the standard tests described herein or using other similar tests which are well known in the art.

Mammal and patient covers warm blooded mammals that are typically under medical care (e.g., humans and domesticated animals). Examples of mammals include (a) feline, canine, equine, bovine, and human and (b) human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; (c) relieving the disease-state, e.g., causing regression of the disease state until a desired endpoint is reached; and/or (d) eliminating the disease-state, e.g., causing cessation of the disease state and/or its effects. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, thane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat an indication listed herein. "Therapeutically effective amount" also includes an amount of the combination of compounds claimed that is effective to treat the desired indication. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Specific and preferred values listed for radicals, substituents, and ranges, are for illustration only; they do not exclude other defined values or other values within defined ranges for the radicals and substituents.

Synthesis

The compounds of the present invention can be prepared by the methods described in US2005/0065341, the contents of which are incorporated herein by reference.

The compounds of the present invention can also be prepared by the methods described in P. J. Scammells, et al., *J. Med. Chem.* 37, 2704-2712 (1994). A diamino-1,3-disubstituted uracil is acylated with 6-chloronicotinoyl chloride in pyridine at 5° C. to provide the compounds of Formula (5a). The resulting amide (5a) is cyclized by refluxing in an aqueous sodium hydroxide solution to provide the compound A. 6-Chloronicotinoyl chloride is prepared by refluxing 6-hydroxynicotinic acid in thionyl chloride using DMF as the catalyst as shown in Reaction Scheme 1.

Compound A can be alkylated with alkyl bromide or iodide to provide compounds of Formula A¹. Compounds A or A¹ react with substituted amine at 150-160° C. in a pressure tube to give compounds of Formula B or B¹. Compounds of Formula B¹ where R⁴ is hydroden can react with acyl chloride to afford compounds where R⁴ is —C(O)R⁶ (C).
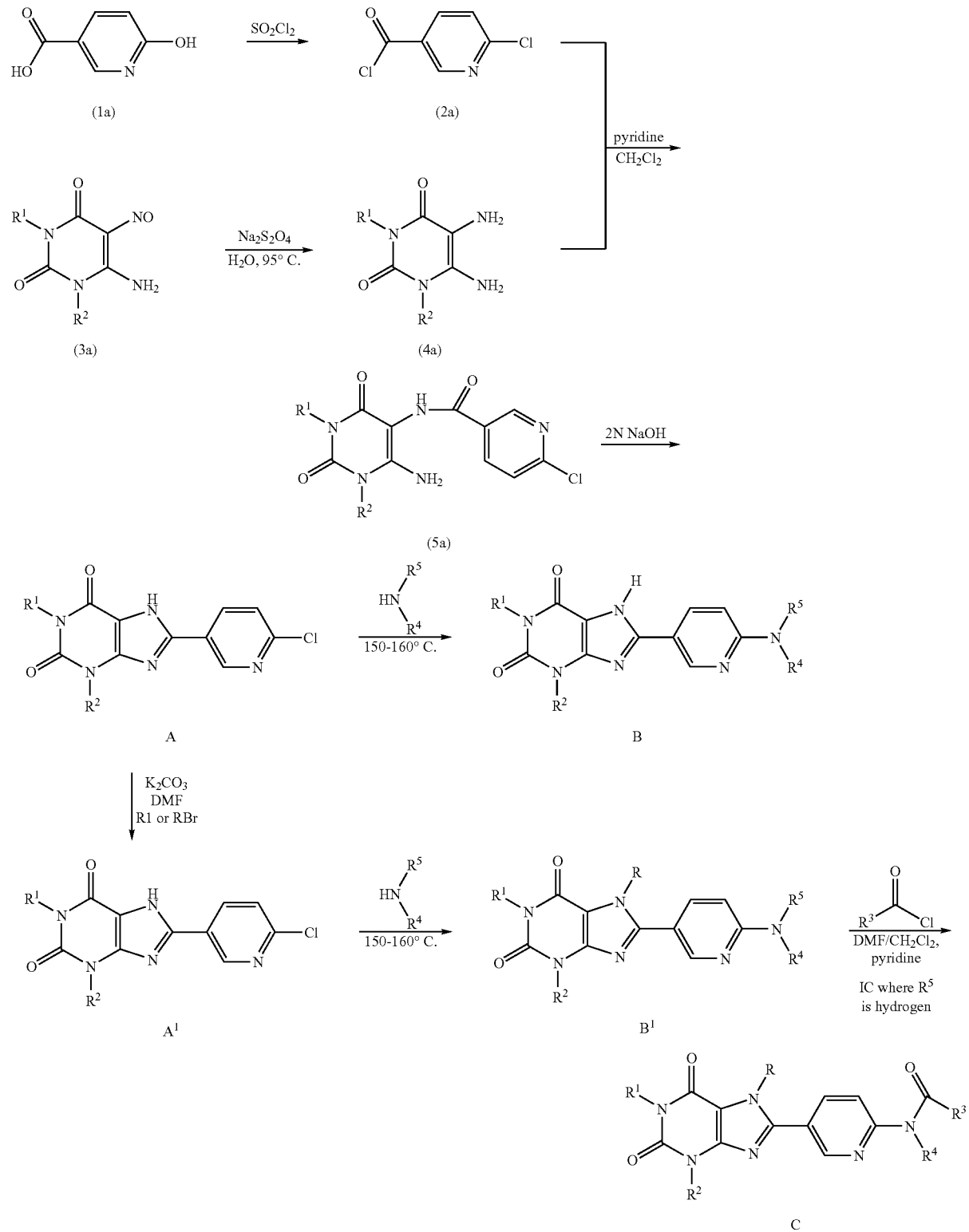

The following abbreviations have been used herein:
[$^{125}$I]ABA [$^{125}$I]N$^6$-(4-aminobenzyl)-adenosine
$^{125}$I-ABOPX $^{125}$I-3-(4-amino-3-iodobenzyl)-8-oxyacetate-1-propyl-xanthine
AR adenosine receptor
CGS 21680 2-[4-[(2-carboxyethyl)phenyl]ethyl-amino]-5N—N-ethylcarbamoyl adenosine
CPX 8-cyclopentyl-1,3-dipropylxanthine
DMEM Dulbecco modified eagle medium
DMF N,N-dimethylformamide
DMSO dimethylsulfoxide
EDTA ethylenediaminetetraacetate
HEK cells human embryonic kidney cells
$K_i$ equilibrium inhibition constant
NECA 5'-(N-ethylcarbamoyl)adenosine
R-PIA R—N$^6$-phenylisopropyladenosine
TEA triethylamine
TLC Thin layer chromatography
ZM 241385 4-(2-[7-amino-2-{furyl}{1,2,4}triazolo {2,3-a}{1,3,5}triazin-5-ylaminoethyl)phenol The compounds of the present invention can be formulated as pharmaceutical compositions and administered to a mammalian host, such as a human patient in a variety of forms adapted to the chosen route of administration, e.g., orally or parenterally, by intravenous, intramuscular, topical, inhalation or subcutaneous routes. Exemplary pharmaceutical compositions are disclosed in "Remington: The Science and Practice of Pharmacy", A. Gennaro, ed., 20th edition, Lippincott, Williams & Wilkins, Philadelphia, Pa.

Thus, the present compounds may be systemically administered, e.g., orally, in combination with a pharmaceutically acceptable excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from (a) about 0.1-25 wt % and (b) about 0.5-10 wt %. The concentration in a semi-solid or solid composition such as a gel or a powder will be (a) about 0.1-5 wt % and (b) about 0.5-2.5 wt %.

The amount of the compound or an active salt or derivative thereof, required for use in treatment will vary not only with the particular compound or salt selected but also with the route of administration, the nature of the condition being treated, and the age and condition of the patient and will be ultimately at the discretion of the attendant physician or clinician. In general, however, a suitable dose will be in the range of from (a) about 1.0-100 mg/kg of body weight per day, (b) about 10-75 mg/kg of body weight per day, and (c) about 5-20 mg per kilogram body weight per day.

The compound can be conveniently administered in unit dosage form; e.g., tablets, caplets, etc., containing (a) about 4-400 mg, (b) about 10-200 mg, and (c) about 20-100 mg of active ingredient per unit dosage form.

Ideally, the active ingredient should be administered to achieve peak plasma concentrations of the active compound of from (a) about 0.02-20 µM, (b) about 0.1-10 µM, and (c) about 0.5-5 µM. These concentrations may be achieved, for example, by the intravenous injection of a 0.005-0.5% solution of the active ingredient, or orally administered as a bolus containing about 4-400 mg of the active ingredient.

The compounds of the invention can also be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences Volumes 16 (1980) or 18 (1990) Mack Publishing Co.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

All patents, patent applications, books and literature cited in the specification are hereby incorporated by reference in their entirety. In the case of any inconsistencies, the present disclosure, including any definitions therein will prevail.

The invention has been described with reference to various specific and preferred embodiments and techniques. However, it should be understood that many variations and modifications may be made while remaining within the spirit and scope of the invention.

EXAMPLES

Pharmacology

The ability of compounds of the invention to act as an $A_{2B}$ adenosine receptor antagonists may be determined using pharmacological models which are well known to the art or using test procedures described below.

The rat $A_{2B}$ receptor cDNA was subcloned into the expression plasmid pDoubleTrouble using techniques described in Robeva, A. et al., *Biochem. Pharmacol.*, 51, 545-555 (1996). The plasmid was amplified in competent JM109 cells and plasmid DNA isolated using Wizard Megaprep columns (Promega Corporation, Madison, Wis.). $A_{2B}$ adenosine receptors were introduced into HEK-293 cells by means of Lipofectin as described in Felgner, P. L. et al., *Proc. Natl. Acad. Sci. USA*, 84, 7413-7417 (1987).

Cell Culture

Transfected HEK cells were grown under 5% $CO_2$/95% $O_2$ humidified atmosphere at a temperature of 37° C. Colonies were selected by growth of cells in 0.6 mg/mL G418. Transfected cells were maintained in DMEM supplemented with Hams F12 nutrient mixture (1/1), 10% newborn calf serum, 2 mM glutamine and containing 50 IU/mL penicillin, 50 mg/mL streptomycin, and 0.2 mg/mL Geneticin (G418, Boehringer Mannheim). Cells were cultured in 10 cm diameter round plates and subcultured when grown confluent (approximately after 72 hours).

Radioligand Binding Studies

At $A_{2B}$ receptors: Confluent monolayers of HEK-$A_{2B}$ cells were washed with PBS followed by ice cold Buffer A (10 mM HEPES, 10 mM EDTA, pH 7.4) with protease inhibitors (10 µg/mL benzamidine, 100 µM phenylmethanesulfonyl fluoride, and 2 µg/mL of each aprotinin, pepstatin and leupeptin). The cells were homogenized in a Polytron (Brinkmann) for 20 s, centrifuged at 30,000×g, and the pellets washed twice with buffer HE (10 mM HEPES, 1 mM EDTA, pH 7.4 with protease inhibitors). The final pellet was resuspended in buffer HE, supplemented with 10% sucrose and frozen in aliquots at −80° C. For binding assays membranes were thawed and diluted 5-10 fold with HE to a final protein concentration of approximately 1 mg/mL. To determine protein concentrations, membranes, and bovine serum albumin standards were dissolved in 0.2% NaOH/0.01% SDS and protein determined using fluorescamine fluorescence. Stowell, C. P. et al., *Anal. Biochem.*, 85, 572-580 (1978).

Saturation binding assays for rat $A_{213}$ adenosine receptors were performed with [$^3$H]ZM214,385 (17 Ci/mmol, Tocris Cookson, Bristol UK) (Ji, X. et al., *Drug Design Discov.*, 16, 216-226 (1999)) or $^{125}$I-ABOPX (2200 Ci/mmol). To prepare $^{125}$I-ABOPX, 10 µL of 1 mM ABOPX in methanol/1 M NaOH (20:1) was added to 50 µL of 100 mM phosphate buffer, pH 7.3. One or 2 mCi of Na$^{125}$I was added, followed by 10 µL of 1 mg/mL chloramine-T in water. After incubation, 20 minutes at room temperature, 50 µL of 10 mg/mL Na-metabisulfite in water was added to quench the reaction. The reaction mixture was applied to a C18 HPLC column, eluting with a mixture of methanol and 5 mM phosphate, pH 6.0. After 5 mm at 35% methanol, the methanol concentration was ramped to 100% over 15 min. Unreacted ABOPX eluted in 11-12 minutes; $^{125}$I-ABOPX eluted at 18-19 min in a yield of 50-60% with respect to the initial s$^{125}$I.

In equilibrium binding assays the ratio of $^{127}$I/$^{125}$I-ABOPX was 10-20/1. Radioligand binding experiments were performed in triplicate with 20-25 µg membrane protein in a total volume of 0.1 mL HE buffer supplemented with 1 U/mL adenosine deaminase and 5 mM $MgCl_2$. The incubation time was 3 h at 21° C. Nonspecific binding was measured in the presence of 100 µM NECA. Competition experiments were carried out using 0.6 mM $^{125}$I-ABOPX. Membranes were filtered on Whatman GF/C filters using a Brandel cell harvester (Gaithersburg, Md.) and washed 3 times over 15-20 seconds with ice cold buffer (10 mM Tris, 1 mM $MgCl_2$, pH 7.4). $B_{max}$ and $K_D$ values were calculated by Marquardt's nonlinear least squares interpolation for single a site binding models. Marquardt, D. M., *J. Soc. Indust. Appl. Math.*, 11, 431-441.21 (1963). $K_i$ values for different compounds were derived from $IC_{50}$ values as described. Linden, J., *J. Cycl. Nucl. Res.*, 8, 163-172 (1982). Data from replicate experiments are tabulated as means±SEM.

At other Adenosine Receptors: [$^3$H]CPX. Bruns, R. F. et al., *Naunyan-Schmiedeberg's Arch. Pharmacol.*, 335, 59-63 (1987). $^{125}$I-ZM241385 and $^{125}$I-ABA were utilized in radioligand binding assays to membranes derived from HEK-293 cells expressing recombinant rat $A_1$, $A_{2A}$ and $A_3$ ARS, respectively. Binding of [$^3$H]R—N$^6$-phenylisopropyladenosine. Schwabe, U. et al., *Naunyn-Schmiedeberg's Arch. Pharmacol.*, 313, 179-187 (1980). ([$^3$H]R-PIA, Amersham, Chicago, Ill.) to $A_1$ receptors from rat cerebral cortical membranes and of [$^3$H]CGS 21680. Jarvis, M. F. et al., *J. Pharmacol. Exp. Therap.*, 251, 888-893 (1989). (Dupont NEN, Boston, Mass.) to $A_{2A}$ receptors from rat striatal membranes was performed as described. Adenosine deaminase (3 units/mL) was present during the preparation of the brain membranes, in a preincubation of 30 min at 30° C., and during the incubation with the radioligands. All non-radioactive compounds were initially dissolved in DMSO, and diluted with buffer to the final concentration, where the amount of DMSO never exceeded 2%. Incubations were terminated by rapid filtration over Whatman GF/B filters, using a Brandell cell harvester (Brandell, Gaithersburg, Md.). The tubes were rinsed three times with 3 mL buffer each.

At least six different concentrations of competitor, spanning 3 orders of magnitude adjusted appropriately for the $IC_{50}$ of each compound, were used. $IC_{50}$ values, calculated with the nonlinear regression method implemented in (Graph-Pad Prism, San Diego, Calif.), were converted to apparent $K_i$ values as described. Linden, J., *J. Cycl. Nucl. Res.*, 8:163-172 (1982). Hill coefficients of the tested compounds were in the range of 0.8 to 1.1.

Functional Assay

HEK-$A_{2B}$ cells from one confluent T75 flask were rinsed with Ca$^{2+}$ and Mg$^{2+}$-free Dulbecco's phosphate buffered saline (PBS) and then incubated in Ca$^{2+}$ and Mg$^{2+}$-free HBSS with 0.05% trypsin and 0.53 mM EDTA until the cells detached. The cells were rinsed twice by centrifugation at 250×g in PBS and resuspended in 10 mL of HBSS composed of 137 mM NaCl, 5 mM KCl, 0.9 mM MgSO$_4$, 1.4 mM CaCl$_2$, 3 mM NaUCO$_3$, 0.6 mM Na$_2$HPO$_4$, 0.4 mM KH$_3$PO$_4$, 5.6 mM glucose, and 10 mM HEPES, pH 7.4 and the Ca$^{2+}$-sensitive fluorescent dye indo-1-AM (5 µM) 37° C. for 60 min. The cells were rinsed once and resuspended in 25 mL dye-free HBSS supplemented with 1 U/ml adenosine deaminase and held at room temperature. Adenosine receptor antagonists prepared as 100× stocks in DMSO or vehicle was added and the cells and transferred to a 37° C. bath for 2 minutes. Then the cells (1 million in 2 ml) were transferred to a stirred cuvette maintained at 37° C. within an Aminco SLM 8000 spectrofluorometer (SML instruments, Urbana Ill.). The ratios of indo-1 fluorescence obtained at 400 and 485 nm (excitation, 332 nm) was recorded using a slit width of 4 nm. NECA was added after a 100 s equilibration period.

Cyclic AMP Accumulation

Cyclic AMP generation was performed in DMEM/HEPES buffer (DMEM containing 50 mM HEPES, pH 7.4, 37° C.). Each well of cells was washed twice with DMEM/HEPES buffer, and then 100 µL adenosine deaminase (final concentration 10 IU/mL) and 100 µL of solutions of rolipram and cilostamide (each at a final concentration of 10 µM) were added, followed by 50 µL of the test compound (appropriate concentration) or buffer. After 15 minutes, incubation at 37° C. was terminated by removing the medium and adding 200 µL of 0.1 M HCl. Acid extracts were stored at −20° C. until assay. The amounts of cyclic AMP were determined following a protocol which utilized a cAMP binding protein (PKA) [van der Wenden et al., 1995], with the following minor modifications. The assay buffer consisted of 150 mM K$_2$HPO$_4$/10 nM EDTA/0.2% BSA FV at pH 7.5. Samples (20 mL) were incubated for 90 minutes at 0° C. Incubates were filtered over GF/C glass microfiber filters in a Brandel M-24 Cell Harvester. The filters were additionally rinsed with 4 times 2 mL 150 mM K$_2$HPO$_4$/10 mM EDTA (pH 7.5, 4° C.). Punched filters were counted in Packard Emulsifier Safe scintillation fluid after 2 hours of extraction.

Representative compounds of the present invention have been shown to be active in the above affinity testing.

Synthesis and Characterization

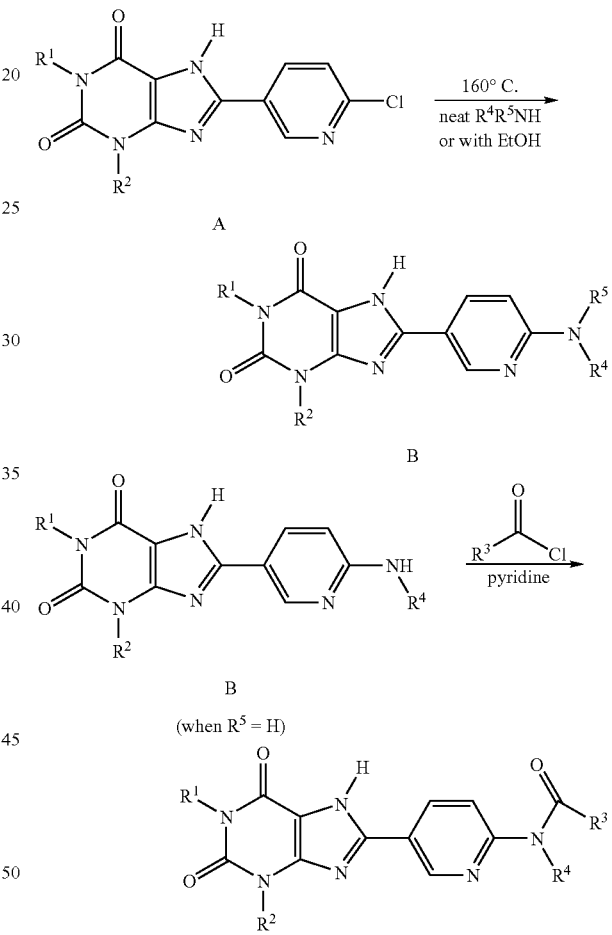

Proton nuclear magnetic resonance spectroscopy was performed on a Varian-300 MHz spectrometer and spectra were taken in DMSO-d$_6$. Unless noted, chemical shifts are expressed as ppm downfield from relative ppm from DMSO (2.5 ppm). Electro-spray-ionization (ESI) mass spectrometry was performed with a ThemroFinnigan LCQ mass spectrometer.

All xanthine derivatives were homogeneous as judged using TLC (Silica gel 60 F$_{254}$, 0.25 mm, aluminium backed, EM Science, Gibbstown, N.J.) and HPLC (Shimadzu) using Varian C18 5 micron analytical column (4.6 mm×150 mm) in linear gradient solvent system, at a flow rate of 1 mL/min. The solvent system used was MeOH (0.1% formic acid):H$_2$O (0.1% formic acid). Peaks were detected by UV absorption at 300 am and 254 nm. NMR and mass spectra were shown to be consistent with the assigned structure.

General Procedures for the Preparation of Chloro Substituted Pyridyl Compounds A 6-Chloronicotinoyl chloride, prepared from 6-hydroxynicotinic acid (1.444 g, 10.4 mmol), in CH$_2$Cl$_2$ (20 mL) was added dropwise to a solution of 5,6-diamino-1)$_3$-disubstituteduracil (8 mmol) in dry pyridine (8.2 mL) maintained at 5° C. The reaction was warmed to room temperature and stirred for an additional 3 hours. Water (50 mL) was added to quench the reaction. The solvent was evaporated to afford a dark colored oil. The oil was refluxed for 2 h in 2N NaOH (20 mL). After cooling, the pH was carefully adjusted to 7 with concentrated HCl. A solid formed and was collected and washed with water (20 mL), ether (20 mL) and chloroform (20 mL) to provide an off-white solid. The product was used in the next step without further purification.

J=7.8 Hz), 7.68 (d, 1H, J=8.4 Hz), 8.46 (dd, 1H, J$_1$=2.4 Hz, J$_2$=8.4 Hz), 9.07 (d, 1H, J=2.4 Hz).

MS: m/z 346 (M+H)$^+$.

3A: 1,3-Diallyl-8-(6-chloro-3-pyridyl)xanthine $^1$H NMR (DMSO, d$_6$): 4.56 (d, 2H, J=5.1 Hz), 4.70 (d, 2H, J=5.1 Hz), 5.15 (m, 4H), 5.98 (m, 2H), 7.74 (d, 1H, J=8.4 Hz), 8.50 (dd, 1H, J$_1$=2.4 Hz, J$_2$=8.4 Hz), 9.12 (d, 1H, J=2.4 Hz).

MS: m/z 344 (M+H)$^+$.

General Procedures for the Preparation of Amino Substituted Pyridyl Compounds B

Compound A (40 mg) and the corresponding substituted amine (0.5 mL or 0.5 g) were put in a pressure tube. (Ethanol, 4 mL, was added as the solvent if the amine is a solid.)

The pressure tube was flushed with argon, sealed and stirred at 160° C. for 48-60 h. After cooling, ether (10 mL) was added. The resulting solid was collected and purified by silica gel column or preparative TLC (Solvent A: CH$_2$Cl$_2$: MeOH=20: 1 to 10: 1 or Solvent B: CH$_2$Cl$_2$: MeOH: TEA=20: 1: 0.1 to 4: 1: 0.1).

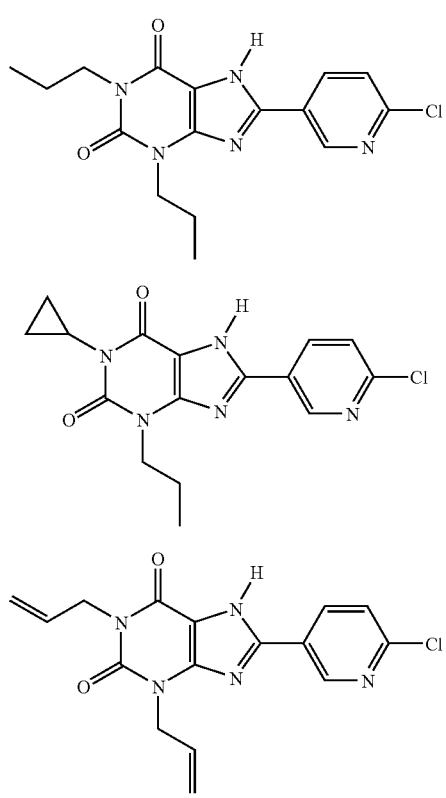

1A: 1,3-Dipropyl-8-(6-chloro-3-pyridyl)xanthine $^1$H NMR (DMSO, d$_6$): δ 0.89 (m, 6H), 1.59 (m, 2H), 1.73 (m, 2H), 3.88 (t, 2H, J=7.2 Hz), 4.00 (t, 2H, J=7.2 Hz), 7.68 (d, 1H, J=8.4 Hz), 8.50 (dd, 1H, J$_1$=2.4 Hz, J$_2$=8.4 Hz), 9.07 (d, 1H, J=2.4 Hz).

MS: m/z 348 (M+H)$^+$.

2A: 1-Cyclopropyl-3-propyl-8-(6-chloro-3-pyridyl)xanthine $^1$H NMR (DMSO, d$_6$): δ 0.72 (m, 2H), 0.91 (t, 3H, J=7.8 Hz), 1.03 (m, 2H), 1.72 (m, 2H), 2.63 (m, 1H), 3.98 (t, 2H,

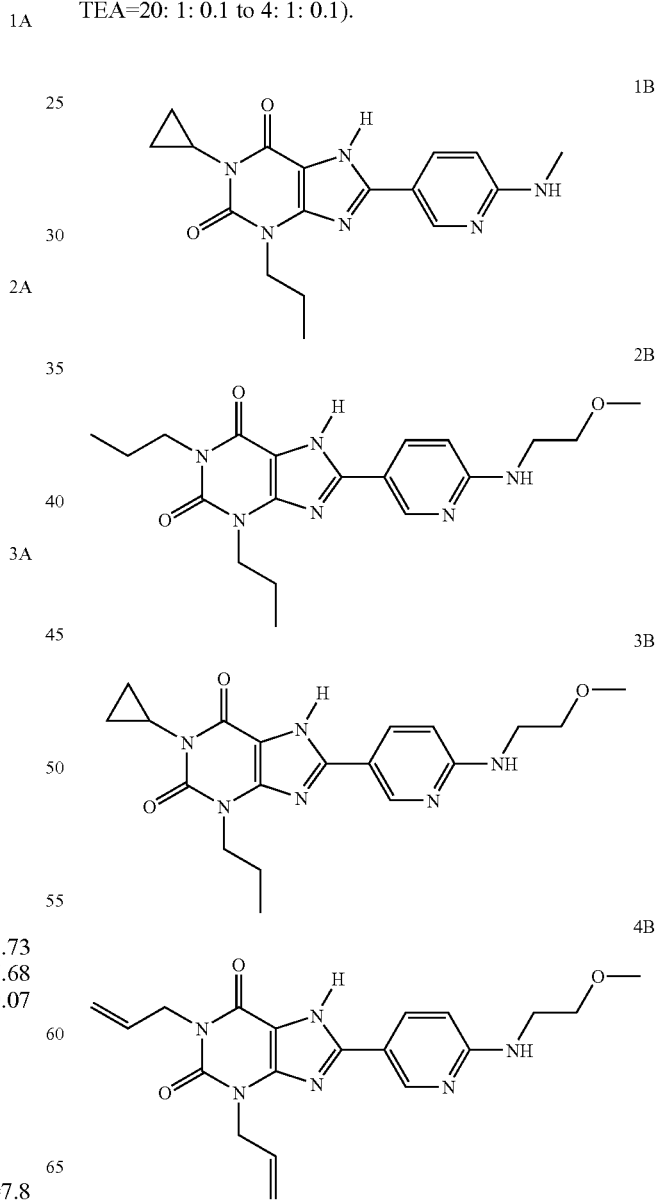

-continued
5B
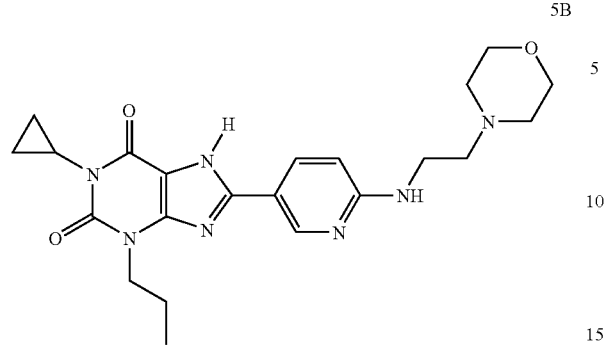
6B
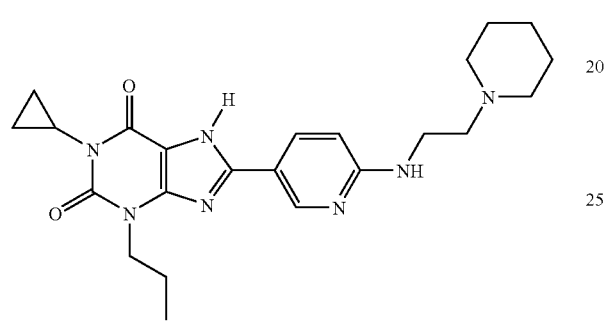
7B
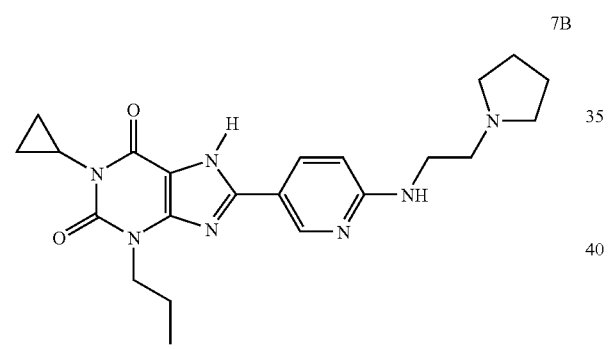
8B
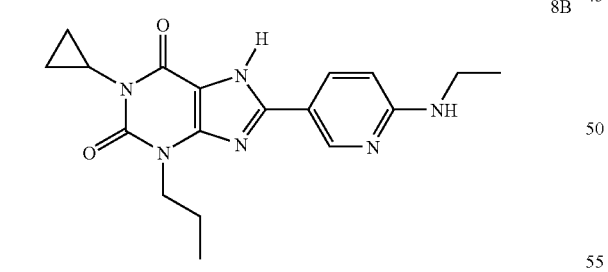
9B
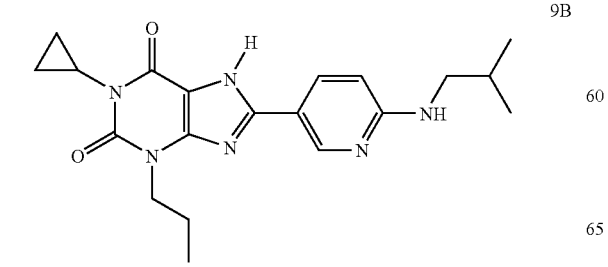
-continued
10B
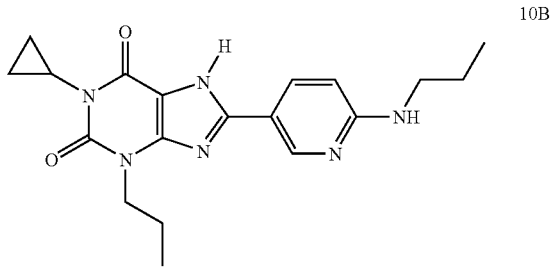
11B
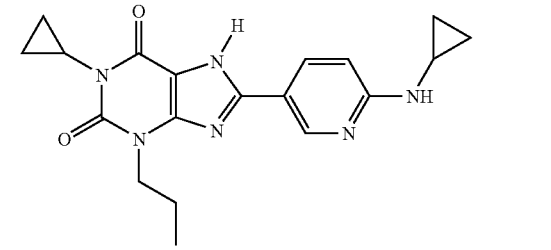
12B
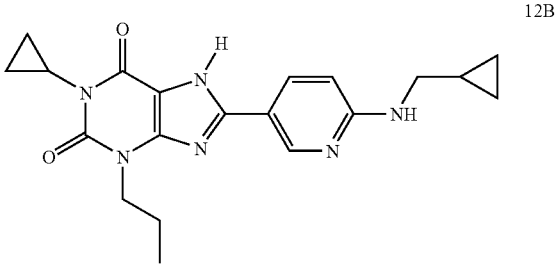
13B
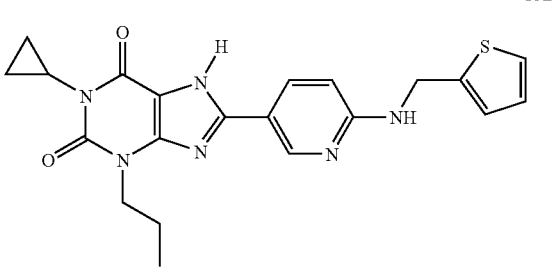
14B
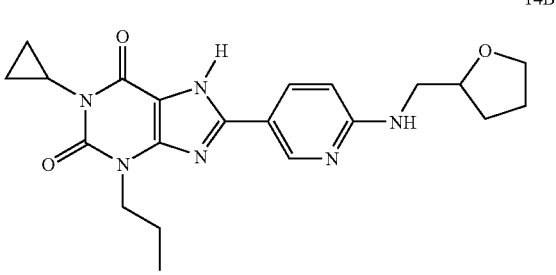
15B
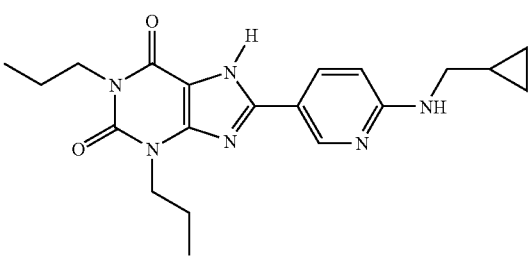

-continued

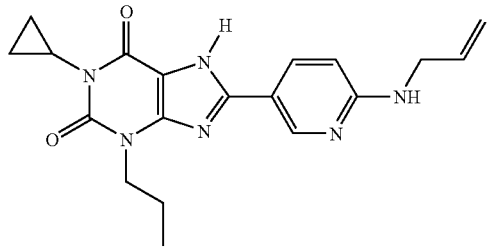

16B

17B

18B

19B

1B: 1-Cyclopropyl-3-propyl-8-[6-methylamino-3-pyridyl]xanthine

¹H NMR (DMSO, d₆): 0.72 (m, 2H), 0.91 (t, 3H, J=7.5 Hz), 1.03 (m, 2H), 1.71 (m, 2H), 2.62 (m, 1H), 2.81 (d, 3H, J=4.5 Hz), 3.96 (t, 2H, J=7.5 Hz), 6.52 (d, 1H, J=9.0 Hz), 7.07 (d, 1H, J=4.5 Hz), 8.01 (dd, 1H, J₁=2.4 Hz, J₂=9.0 Hz), 8.73 (d, 1H, J=2.4 Hz).

MS: m/z 341 (M+H)⁺.

2B: 1,3-Dipropyl-8-[6-(2-methoxyethyl)amino-3-pyridyl]xanthine

¹H NMR (DMSO, d₆): δ 0.93 (m, 6H), 1.63 (m, 2H), 1.78 (m, 2H), 3.38 (s, 3H), 3.53 (s, 4H), 3.91 (t, 2H, J=7.5 Hz), 4.05 (t, 2H, J=7.5 Hz), 6.65 (d, 1H, J=8.7 Hz), 7.24 (s(br), 1H), 8.06 (dd, 1H, J₁=2.4 Hz, J₂=8.7 Hz), 8.71 (d, 1H, J=2.4 Hz).

MS: m/z 387 (M+H)⁺.

3B: 1-Cyclopropyl-3-propyl-8-[6-(2-methoxyethyl)amino-3-pyridyl]xanthine

¹H NMR (DMSO, d₆): 0.74 (m, 2H), 0.94 (t, 3H, J=7.5 Hz), 1.06 (m, 2H), 1.75 (m, 2H), 2.65 (m, 1H), 3.32 (s, 3H), 3.52 (s, 4H), 4.00 (t, 2H, J=7.5 Hz), 6.64 (d, 1H, J=8.7 Hz), 7.23 (s(br), 1H), 8.04 (dd, 1H, J₁=2.4 Hz, J₂=8.7 Hz), 8.76 (d, 1H, J=2.4 Hz).

MS: m/z 385 (M+H)⁺.

4B: 1,3-Diallyl-8-[6-(2-methoxyethyl)amino-3-pyridyl]xanthine

¹H NMR (DMSO, d₆): 3.32 (s, 3H), 3.52 (s, 4H), 4.55 (d, 2H, J=5.1 Hz), 4.68 (d, 2H, J₁=5.1 Hz), 5.15 (m, 4H), 5.95 (m, 2H), 6.64 (d, 1H, J=9.0 Hz), 7.25 (s(br), 1H), 8.05 (dd, 1H, J₁=2.4 Hz, J₂=9.0 Hz), 8.77 (d, 1H, J=2.4 Hz).

MS: m/z 383 (M+H)⁺.

5B: 1-Cyclopropyl-3-propyl-8-[6-(2-morpholinoethyl)amino-3-pyridyl]xanthine

¹H NMR (DMSO, d₆): 0.74 (m, 2H), 0.94 (t, 3H, J=7.5 Hz), 1.06 (m, 2H), 1.75 (m, 2H), 2.46 (t, 4H, J=4.5 Hz), 2.52(m, 2H), 2.65 (m, 1H), 3.46 (m, 2H), 3.63 (t, 4H. J=4.5 Hz), 4.00 (t, 2H, J=7.2 Hz), 6.62 (d, 1H, J=8.7 Hz), 7.23 (t, 1H, J=5.4 Hz), 8.04 (dd, 1H, J₁=2.4 Hz, J₂=8.7 Hz), 8.75 (d, 1H, J=2.4 Hz).

MS: m/z 440 (M+H)⁺.

6B: 1-Cyclopropyl-3-propyl-8-[6-(2-(piperidin-1-yl)ethylamino-3-pyridyl]xanthine ¹H NMR (DMSO, d₆): 0.74 (m, 2H), 0.94 (t, 3H, J=7.5 Hz), 1.07 (m, 2H), 1.44 (m, 2H), 1.57 (m, 4H), 1.75 (m, 2H), 2.51 (m, 6H), 2.65 (m, 1H), 3.48 (m, 2H), 4.00 (t, 2H, J=7.2 Hz), 6.63 (d, 1H, J=9.0 Hz), 7.05 (t, 1H), 8.05 (dd, 1H, J₁=2.4 Hz, J₂=9.0 Hz), 8.76 (d, 1H, J=2.4 Hz).

MS: m/z 438 (M+H)⁺.

7B: 1-Cyclopropyl-3-propyl-8-[6 (2-(pyrrolidin-1-yl)ethylamino)-3-pyridyl]xanthine MS: m/z 424 (M+H)⁺.

General Procedures for the Preparation of Amide Compounds (1-6)

The amino substituted pyridyl compound B (50 mg) was dissolved in pyridine (25 mg) at 80-100° C. After cooling to room temperature, the desired acid chloride (4-6 equivalents) was added at room temperature. The mixture was stirred at room temperature for 24-60 h. The reaction was quenched with ice and the solvent was removed and the residue was purified by silica gel column (CH₂Cl₂: MeOH=96: 4) to give compound 1-6 at 60-80% yield.

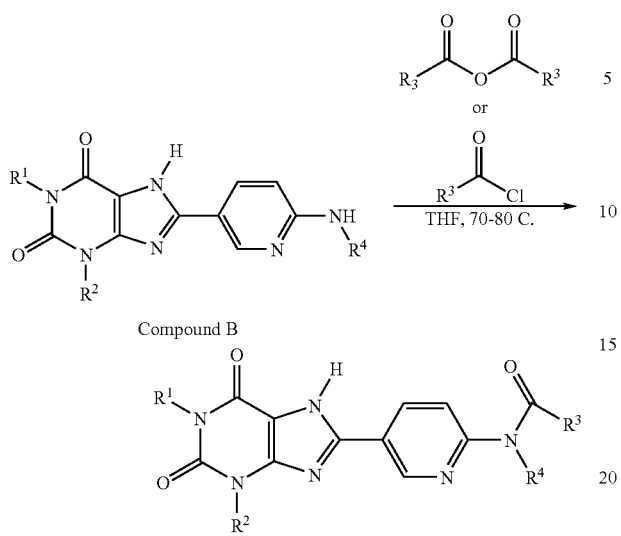

Compound B

General Procedures for the Preparation of Amide Substituted Pyridyl Compounds 42-45:

Compound B (50 mg) and the corresponding anhydride or acid chloride (>10 eq) were placed in a pressure vessel and dissolved in dry pyridine (~5-10 mls). For anhydride reactions, DMAP was added in catalytic amounts. The pressure vessel was flushed with nitrogen, sealed and stirred at 80° C. for 24-72 h. After cooling, the mixture was concentrated in vacuo and purified by gradient silica gel chromatography or preparative HPLC.

1: 6-Chloro-N-[5-(1-cyclopropyl-2,6-dioxo-3-propyl-2,3,6,7-tetrahydro-1H-purin-8-yl)-pyridin-2-yl]-N-(2-pyridin-2-yl-ethyl)-nicotinamide Example 1 was made by methods similar to those described above.

HPLC condition: MeOH 40-95% gradient in water over 10 minutes then MeOH 95%. Retention Time: 7.81 min.
MS: m/z 571.23 (M+H)⁺.

$^1$H NMR (DMSO, d$_6$): δ 0.75 (m, 3H), 0.928 (t, 3H, J=7.5 Hz), 1.08 (q, 2H, J=7.2 Hz), 1.74 (q, 3H, J=7.5 Hz), 2.69 (m, 1H), 3.15 (t, 1H, J=7.5 Hz), 4.00 (t, 2H, 6.6 Hz), 4.42 (t, 2H, J=6.6 Hz), 7.23 (m, 1H), 7.31 (m, 1H), 7.51 (d, 1H, J=8.1 Hz), 7.73 (m, 2H), 8.31 (m, 2H), 8.48 (m, 1H), 9.07 (d, 1H, J=2.1).

2: N-[5-(1-Cyclopropyl-2,6-dioxo-3-propyl-2,3,6,7-tetrahydro-1H-purin-8-yl)-pyridin-2-yl]-N-(3-morpholin-4-yl-propyl)-benzamide HPLC condition: MeOH 40-95% gradient in water over 10 minutes then MeOH 95%. Retention Time: 10.12 min.
MS: m/z 558.21 (M+H)⁺.

3: N-[5-(1-Cyclopropyl-2,6-dioxo-3-propyl-2,3,6,7-tetrahydro-1H-pyridin-8-yl)-pyridin-2-yl]-N-(3-morpholin-4-yl-propyl)-6-trifluoromethyl-nicotinamide HPLC condition: MeOH 40-95% gradient in water over 10 minutes then MeOH 95%. Retention Time: 10.01 min.
MS: m/z 627.33 (M+H)⁺.

4: N-[5-(1-Cyclopropyl-2,6-dioxo-3-propyl-2,3,6,7-tetrahydro-1H-purin-8-yl)-pyridin-2-yl-]2,2-dimethyl-N-(6-trifluoromethyl-pyridin-3-ylmethyl)-propionamide

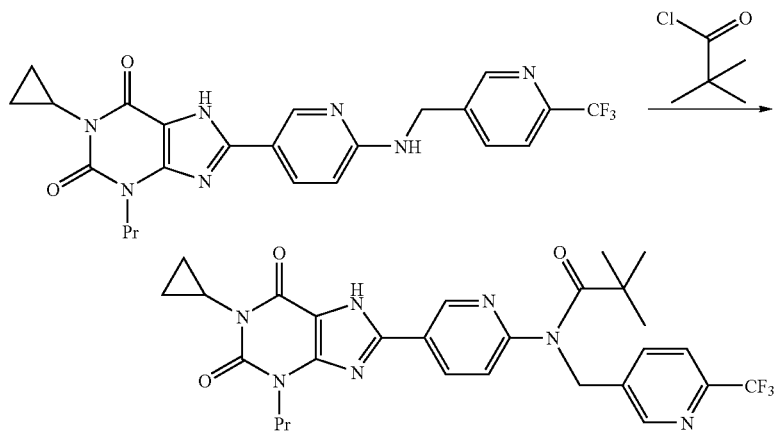

8-(6-((6-(trifluoromethyl)pyridin-3-yl)methylamino)pyridin-3-yl)-1-cyclopropyl-3-propyl-1H-purine-2,6(3H,7H)-dione (35 mg, 0.07 mmol) was dissolved in pyridine (5 ml) at 60° C. After cooling, pivaloyl chloride (100 mg, 0.83 mmol) was added. The mixture was stirred at room temperature for 24 h. After quenching with ice, the mixture was evaporated and purified by silica gel column to give product (4).

HPLC condition: MeOH 40-95% gradient in water over 10 minutes then MeOH 95%. Retention Time=11.3 min.
MS: m/z 570 (M+H)⁺.

5: N-[5-(1-Cyclopropyl-2,6-dioxo-3-propyl-2,3,6,7-tetrahydro-1H-purin-8-yl)-pyridin-2-yl]-N-cyclopropylmethyl-4-fluoro-benzamide HPLC condition: MeOH 40-95% gradient in water over 10 minutes then MeOH 95%. Retention Time=10.75 min.
MS: m/z 503 (M+H)⁺.

6: N-[5-(1-Cyclopropyl-2,6-dioxo-3-propyl-2,3,6,7-tetrahydro-1H-purin-8-yl)-pyridin-2-yl]-N-cyclopropylmethyl-3,4-difluoro-benzamide HPLC condition: MeOH 20-95% gradient in water over 4 minutes at 40° C., 6 minutes total. Retention Time=3.75 min. MS: m/z 521.31 (M+11)$^+$.

Numerous modifications and variations of the present invention are possible in light of the above teachings. It is therefore to be understood that within the scope of the appended claims, the invention may be practiced otherwise that as specifically described herein.

What is claimed is:

1. A compound selected from the group:

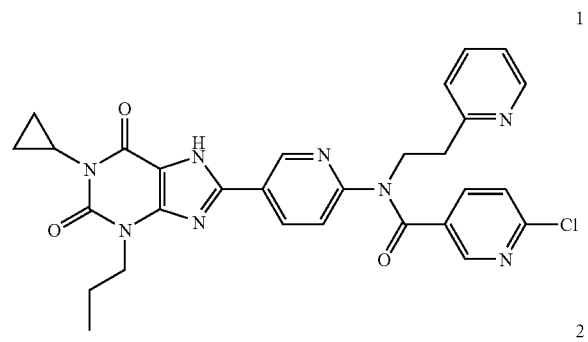

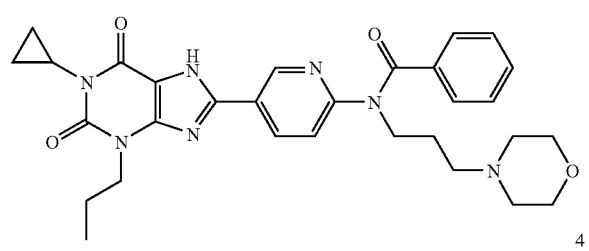

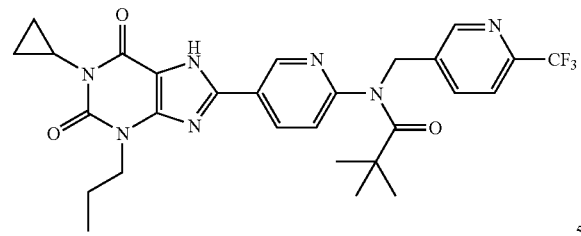

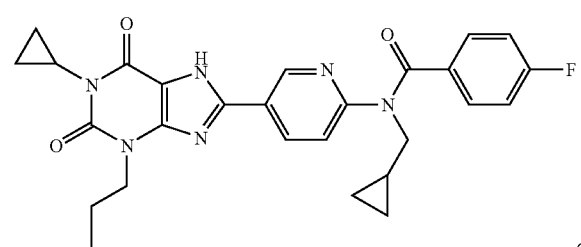

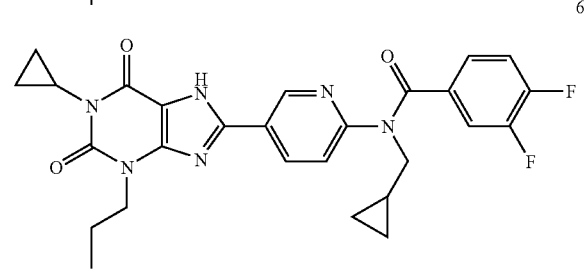

or a pharmaceutically acceptable salt thereof.

2. A pharmaceutical composition comprising:
   (a) a therapeutically effective amount of a compound of claim 1; and
   (b) a pharmaceutically acceptable excipient.
3. A method for treating asthma comprising administering an effective amount of a compound claim 1 to a mammal in need of such treatment.
4. A method for treating diarrhea, insulin resistance, and diabetic retinopathy, comprising administering an effective amount of a compound claim 1 or a pharmaceutically acceptable salt thereof to a mammal in need of such treatment.
5. A compound of claim 1, wherein the compound is:

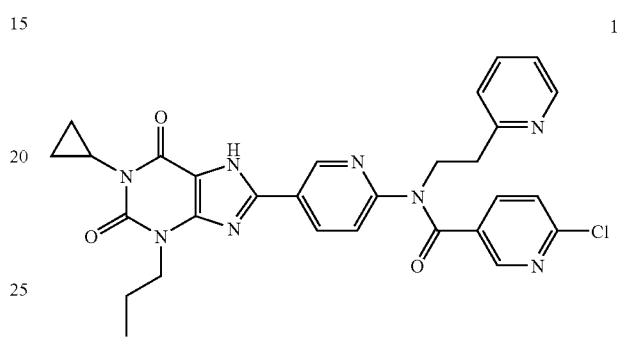

or a pharmaceutically acceptable salt thereof.

6. A pharmaceutical composition comprising:
   (a) a therapeutically effective amount of a compound of claim 5; and
   (b) a pharmaceutically acceptable excipient.
7. A compound of claim 1, wherein the compound is:

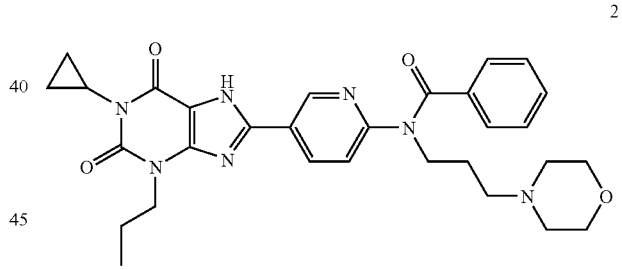

or a pharmaceutically acceptable salt thereof.

8. A pharmaceutical composition comprising:
   (a) a therapeutically effective amount of a compound of claim 7; and
   (b) a pharmaceutically acceptable excipient.
9. A compound of claim 1, wherein the compound is:

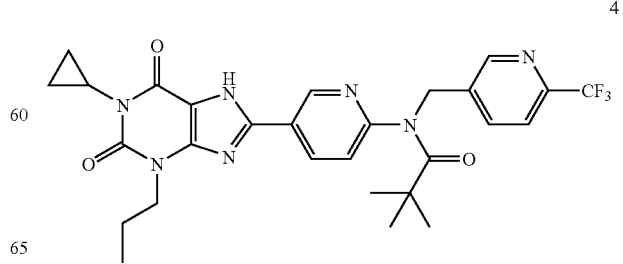

or a pharmaceutically acceptable salt thereof.

10. A pharmaceutical composition comprising:
(a) a therapeutically effective amount of a compound of claim 9; and
(b) a pharmaceutically acceptable excipient.

11. A compound of claim 1, wherein the compound is:

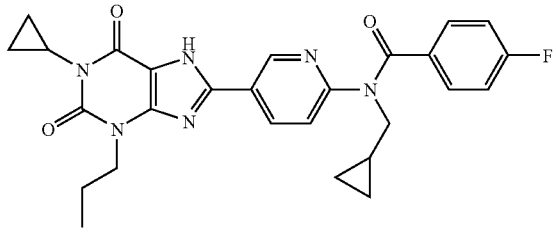

or a pharmaceutically acceptable salt thereof.

12. A pharmaceutical composition comprising:
(a) a therapeutically effective amount of a compound of claim 11; and
(b) a pharmaceutically acceptable excipient.

13. A compound of claim 1, wherein the compound is:

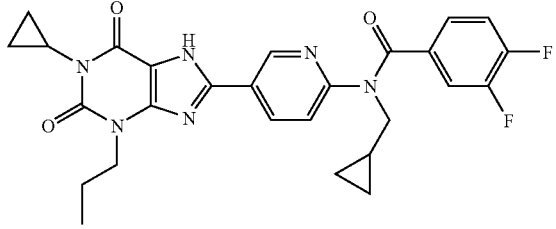

or a pharmaceutically acceptable salt thereof.

14. A pharmaceutical composition comprising:
(a) a therapeutically effective amount of a compound of claim 13; and
(b) a pharmaceutically acceptable excipient.

15. A method for treating asthma, comprising administering an effective amount of a compound claim 5 to a mammal in need of such treatment.

16. A method for treating diarrhea, insulin resistance, and diabetic retinopathy, comprising administering an effective amount of a compound claim 5 or a pharmaceutically acceptable salt thereof to a mammal in need of such treatment.

17. A method for treating asthma, comprising administering an effective amount of a compound claim 7 to a mammal in need of such treatment.

18. A method for treating diarrhea, insulin resistance, and diabetic retinopathy, comprising administering an effective amount of a compound claim 7 or a pharmaceutically acceptable salt thereof to a mammal in need of such treatment.

19. A method for treating asthma, comprising administering an effective amount of a compound claim 9 to a mammal in need of such treatment.

20. A method for treating diarrhea, insulin resistance, and diabetic retinopathy, comprising administering an effective amount of a compound claim 9 or a pharmaceutically acceptable salt thereof to a mammal in need of such treatment.

21. A method for treating asthma, comprising administering an effective amount of a compound claim 11 to a mammal in need of such treatment.

22. A method for treating diarrhea, insulin resistance, and diabetic retinopathy, comprising administering an effective amount of a compound claim 11 or a pharmaceutically acceptable salt thereof to a mammal in need of such treatment.

23. A method for treating asthma, comprising administering an effective amount of a compound claim 13 to a mammal in need of such treatment.

24. A method for treating diarrhea, insulin resistance, and diabetic retinopathy, comprising administering an effective amount of a compound claim 13 or a pharmaceutically acceptable salt thereof to a mammal in need of such treatment.

* * * * *